US00PP25429P3

(12) United States Plant Patent
Unger

(10) Patent No.: US PP25,429 P3
(45) Date of Patent: Apr. 7, 2015

(54) *OENOTHERA* PLANT NAMED 'UNG OEN01'

(50) Latin Name: *Oenothera hybrida*
Varietal Denomination: UNG OEN01

(71) Applicant: Moerheim New Plant B.V., Leimuiderbrug (NL)

(72) Inventor: Helmut E. Unger, Worms (DE)

(73) Assignee: Moerheim New Plant B.V., Leimuiderbrug (NL)

( * ) Notice: Subject to any disclaimer, the term of this patent is extended or adjusted under 35 U.S.C. 154(b) by 304 days.

(21) Appl. No.: 13/694,050

(22) Filed: Oct. 24, 2012

(65) Prior Publication Data

US 2014/0013476 P1 Jan. 9, 2014

(30) Foreign Application Priority Data

Jul. 9, 2012 (QZ) ..... PBR 20121554

(51) Int. Cl.
*A01H 5/00* (2006.01)

(52) U.S. Cl.
USPC ..... Plt./460

(58) Field of Classification Search
USPC ..... Plt./460
See application file for complete search history.

*Primary Examiner* — Kent L Bell
(74) *Attorney, Agent, or Firm* — Buchanan, Ingersoll & Rooney PC

(57) ABSTRACT

A new *Oenothera hybrida* plant is provided that continuously forms in abundance attractive large pure deep yellow blossoms from spring to autumn. The plant exhibits an annual behavior in the absence of substantial winter hardiness. Good tolerance to heat is displayed in the presence of adequate water. Also, generally good tolerance to disease and pests is displayed. The plant is particularly well suited for providing attractive ornamentation when grown in patio pots, hanging baskets, balcony boxes, mass plantings, etc.

4 Drawing Sheets

Botanical/commercial classification: *Oenothera hybrida*/ Evening Primrose.

Varietal denomination: cv. UNG OEN01.

SUMMARY OF THE INVENTION

The new variety of Evening Primrose plant of the present invention was created at Rheinland Palatinate, Germany, by artificial pollination wherein two parents were crossed which previously had been studied in the hope that they would contribute the desired characteristics. The female parent (i.e., the seed parent) was the proprietary unreleased *Oenothera missouriensis* variety 'O4' (non-patented in the United States). The male parent (i.e., pollen parent) was the proprietary unreleased *Oenothera fruiticosa* variety 'O32' (non-patented in the United States). The parentage of the new variety can be summarized as follows:

'O4'×'O32'.

The seeds resulting from the above pollination were sown and small plants were obtained which were physically and biologically different from each other. Selective study resulted in the identification of a single plant of the new variety.

It was found that the new variety of the present invention exhibits the following combination of characteristics:

(a) exhibits an annual behavior in the absence of substantial winter hardiness,
(b) continuously forms in abundance attractive large pure deep yellow blossoms from spring to autumn,
(c) displays good tolerance to heat in the presence of adequate water,
(d) generally displays good tolerance to disease and pests, and (e) is well suited for providing distinctive attractive ornamentation.

The new cultivar of the present invention well meets the needs of the horticultural industry and can be grown to advantage as an ornamental annual bedding plant. It performs well in patio pots, hanging baskets, balcony boxes, mass plantings, etc. The attractive large deep yellow flowers commonly form on a continuous basis from May to the time of autumn frost. The plant grows well provided adequate water is supplied in a non-excessive quantity. The deep yellow blossom coloration lacks variegation and contrasts nicely with the foliage coloration.

The plant asexually propagates well through the use of softwood cuttings. Rooting commonly is achieved in approximately two weeks. Salable bedding plants can be produced in approximately 2 to 3 months, depending on the pot size and environmental conditions that are encountered.

The new variety can be readily distinguished from its ancestors. More specifically, both of the 'O4' and 'O32' parental plants lack an annual plant character, as well as the formation of large pure deep yellow blossoms, and a continuous flowering character.

Also, the new variety can be readily distinguished from previously available *Oenothera* varieties, such as 'African Sun' (non-patented in the United States), 'INNOENO131' (U.S. Plant Pat. No. 16,393), 'Lishal' (U.S. Plant Pat. No. 18,402), and 'Shimmer' (U.S. Plant Pat. No. 19,663). The 'African Sun' variety forms more linear leaves and smaller flowers, and displays greater hardiness. Also, the 'INNOENO131', 'Lishal' and 'Shimmer' varieties form smaller flowers and are substantially more hardy.

Softwood cutting and tissue culture have been used to asexually propagate the new variety at Rheinland Palatinate, Germany, and at Leimuiderbrug, The Netherlands. It has been found that the distinctive combination of characteristics of the new cultivar is firmly fixed and is reliably transmitted to succeeding generations during such asexual propagation. In The Netherlands, recently propagated plants can be brought to flower in greenhouse production during late April, and subsequently planted outside during May after the risk of frost has subsided. The new variety has been named 'UNG OEN01'.

BRIEF DESCRIPTION OF THE PHOTOGRAPH

The accompanying photographs show typical flowering specimens of the new variety in color as nearly true as it is reasonably possible to make the same in a color illustration of this nature. The plants had been asexually reproduced by softwood cuttings and were being grown at Leimuiderbrug, The Netherlands.

DETAILED DESCRIPTION

Figure 1:
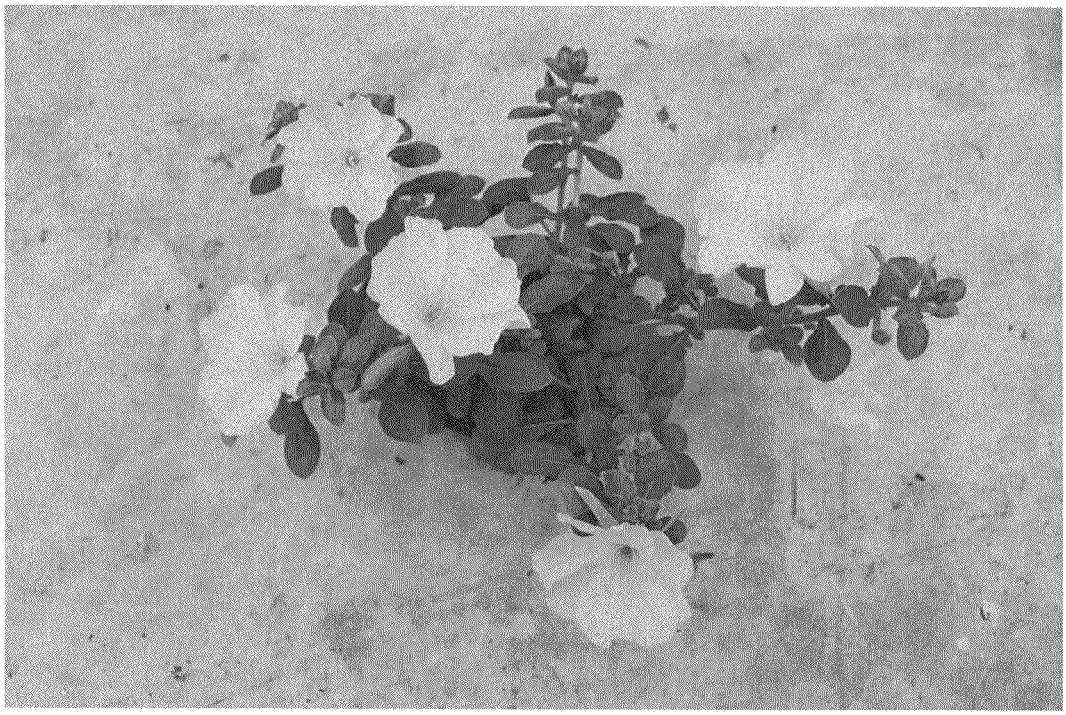
FIG. 1 illustrates in the spring a typical young flowering plant at an age of approximately 2 months while growing in a 10 cm pot.
Figure 2:
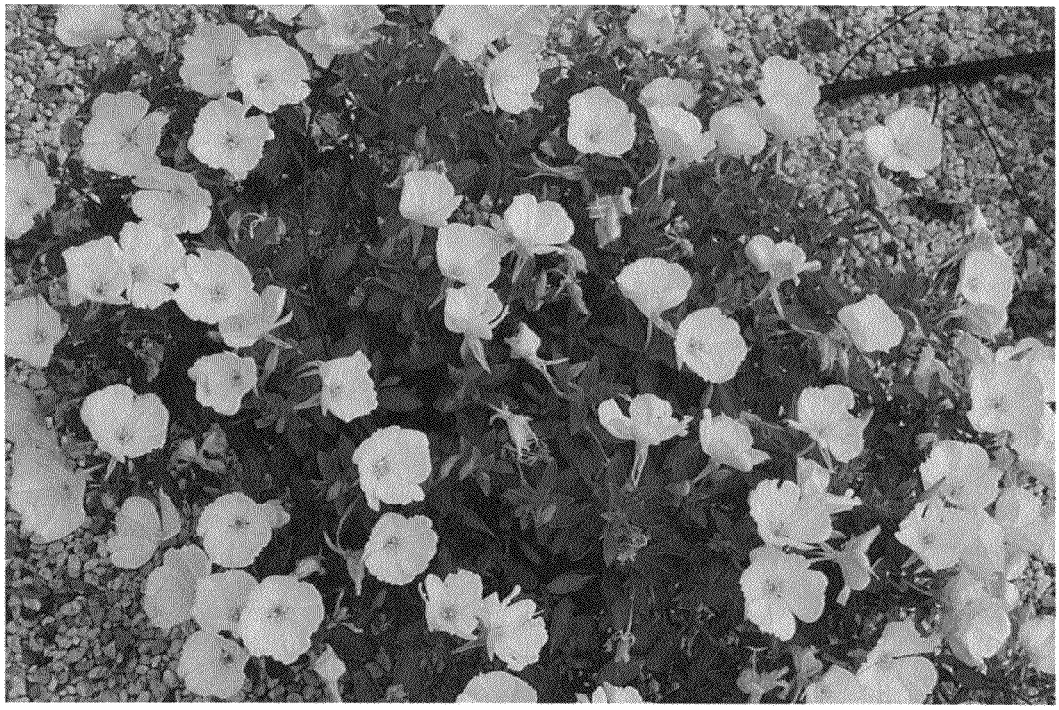
FIG. 2 illustrates a typical mature flowering plant while growing in a larger container.
Figure 3:
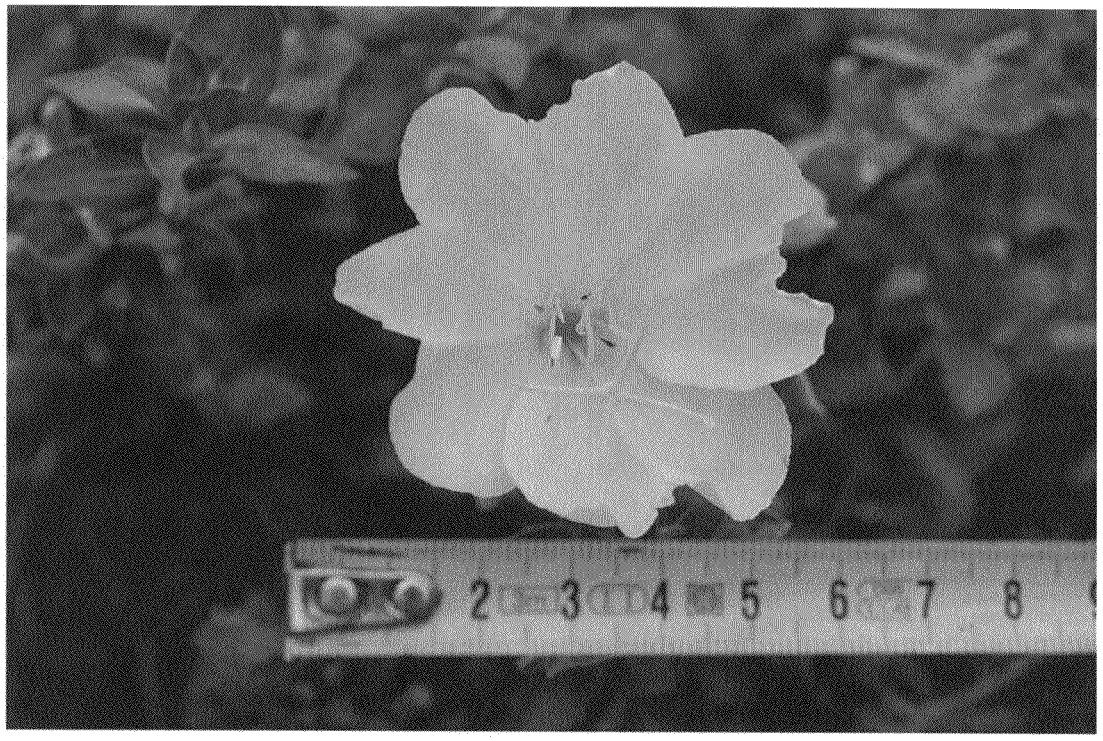
FIG. 3 illustrates a close view of a typical large pure deep yellow fully open flower in which dimensions in centimeters are included for comparative purposes.
Figure 4:
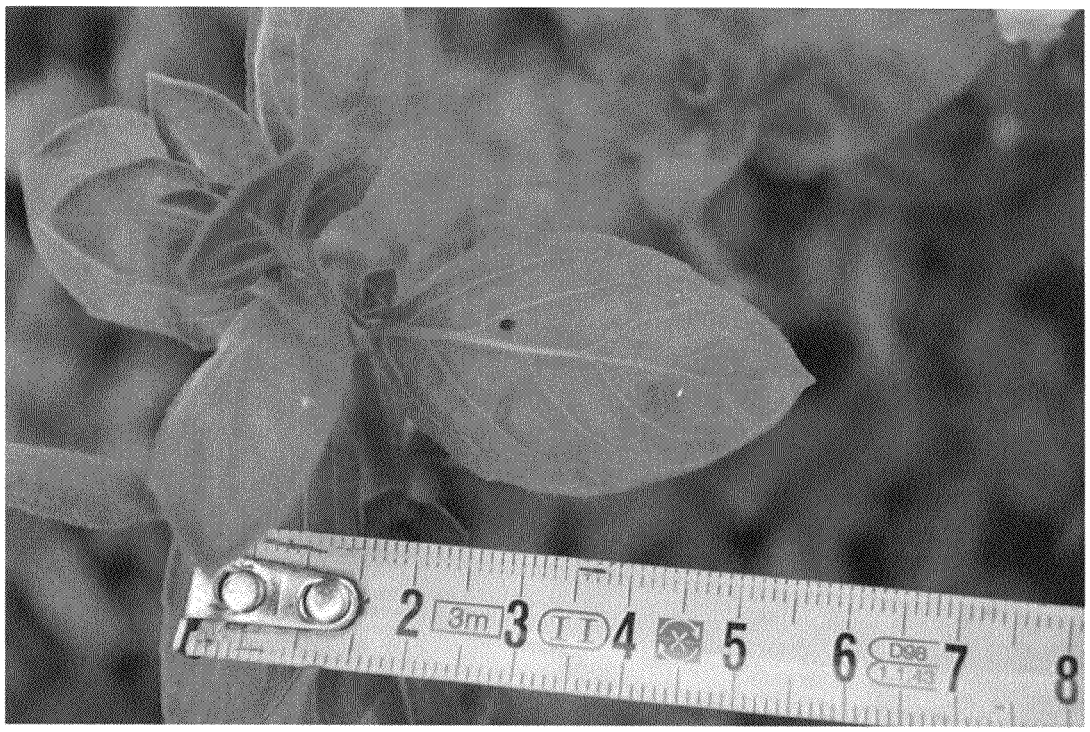
FIG. 4 illustrates a close view of typical foliage in which dimensions in centimeters are included for comparative purposes.

The following is a detailed description of the new variety that was prepared while observing mature plants of the new variety which had been asexually reproduced by the use of softwood cuttings and were growing at Leimuiderbrug, The Netherlands. The chart used in the identification of color is The R.H.S. Colour Chart of The Royal Horticultural Society, London, England (1995 Edition or equivalent).

Botanical classification: *Oenothera hybrida*, 'UNG OEN01'.

Plant:

*Type*.—Annual ornamental plant.

*Height*.—A mature plant after 5 months commonly is approximately 30 cm in height.

*Width*.—A mature plant after 5 months commonly is approximately 100 cm in width.

*Rooting ability*.—Roots commonly are formed on softwood cuttings within approximately 15 days at 20° C.

*Lateral branches*.—Length: commonly approximately 30 cm on average on a typical plant. Diameter commonly approximately 1 cm on average on a typical plant. Internode length: commonly approximately 1 to 2 cm on average on a typical plant. Texture: commonly somewhat rough. Color: near Yellow-Green Group 145A.

Leaves:

*Shape*.—Generally elliptic.

*Length*.—Commonly approximately 3 to 5 cm on average at maturity.

*Width*.—Commonly approximately 1.5 to 2 cm on average at maturity.

*Margins*.—Bear very fine flexible extensions.

*Apex*.—Generally acute to cuspidate.

*Base*.—Generally cuneate to obtuse.

*Texture*.—Slightly undulated, often slightly concave and with a matte finish on both surfaces.

*Leaf color*.—Near Green Group 137C on the upper surface, and near Green Group 134B on the under surface.

*Venation*.—Pinnate-elliptic, with a lighter green midvein of commonly near Yellow-Green Group 145C.

Inflorescence:

*Flowering time*.—Early and continuously from late April to time of first frost in autumn.

*Flower type*.—Solitary terminal and axillary rounded flowers.

*Bud shape*.—Elongated and substantially straight.

*Bud length*.—Commonly approximately 4 cm on average.

*Bud width*.—Commonly approximately 1 cm in diameter on average at the widest point.

*Bud color*.—Commonly near Yellow-Green Group 145A on average.

*Flower quantity*.—Commonly blossoms profusely in abundance with approximately 10 blossoms per lateral branch over a blossoming cycle.

*Flower diameter*.—Large, commonly approximately 6 cm on average.

*Flower depth*.—Commonly approximately 3 to 4 cm on average.

*Flower color*.—Deep clear yellow, near Yellow Group 6A.

*Flower lastingness*.—Commonly one or two days on the plant.

*Petal number*.—Commonly four and not fused.

*Petal shape*.—Somewhat triangular with rounded corners.

*Petal length*.—Commonly approximately 3 to 4 cm on average.

*Petal width*.—Commonly approximately 3 to 4 cm on average.

*Petal texture*.—Smooth on both surfaces.

*Petal color*.—Deep clear yellow, near Yellow Group 6A on both surfaces.

*Petal margin*.—Entire, smooth and commonly somewhat undulated.

*Fragrance*.—None observed.

*Stamen number*.—Typically light.

*Fertility*.—Has not been observed.

*Petiole length*.—Commonly approximately 1 cm on average.

*Petiole diameter*.—Commonly approximately 2 mm on average.

*Petiole texture*.—Somewhat rough.

*Petiole color*.—Near Yellow-Green Group 145A.

*Sepal number*.—Commonly four.

*Sepal shape*.—Elongated and pointed at apex.

*Sepal length*.—Commonly approximately 4 cm on average.

*Sepal width*.—Commonly approximately 1 cm at the widest point.

*Sepal margin*.—Entire, and smooth.

*Sepal texture*.—Somewhat rough on the upper surface.

*Sepal color*.—Near Yellow-Green Group 145A on the upper surface.

Development:

*Blooming*.—Continuously in abundance from late April to autumn at the time of the first frost.

*Resistance to diseases*.—Good, with no particular susceptibility to diseases outdoors even in a dry or rainy climate during observations to date. However, in a too moist rooting environment in a greenhouse, *Botrytis* can occur.

*Hardiness*.—None observed, has not survived when grown at The Netherlands coastal region.

*Resistance to pests*.—Good, with no particular susceptibility to pests outdoors during observations to date. However, under greenhouse growing conditions, some susceptibility to white fly and thrips can occur.

*Resistance to heat*.—Good heat tolerance so long as adequate water is provided.

*Resistance to drought*.—Medium tolerance, with some yellowing of foliage when inadequate water is provided.

Plants of the new 'UNG OEN01' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Oenothera hybrida* plant that exhibits the following combination of characteristics:

(a) exhibits an annual behavior in the absence of substantial winter hardiness, (b) continuously forms in abundance attractive large pure deep yellow blossoms from spring to autumn, (c) displays good tolerance to heat in the presence of adequate water, (d) generally displays good tolerance to disease and pests, and (e) is well suited for providing distinctive attractive ornamentation;

substantially as illustrated and described.

* * * * *